US010765397B2

(12) United States Patent
Komasaka et al.

(10) Patent No.: US 10,765,397 B2
(45) Date of Patent: Sep. 8, 2020

(54) RADIOGRAPHIC IMAGING SYSTEM, RADIOGRAPHIC IMAGING APPARATUS, BATTERY CHARGER, AND METHOD OF INSPECTING WATERPROOF PERFORMANCE

(71) Applicant: KONICA MINOLTA, INC., Chiyoda-ku, Tokyo (JP)

(72) Inventors: Tomonori Komasaka, Tokyo (JP); Ikuma Ota, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/277,742

(22) Filed: Feb. 15, 2019

(65) Prior Publication Data

US 2019/0254621 A1 Aug. 22, 2019

(30) Foreign Application Priority Data

Feb. 19, 2018 (JP) .................................. 2018-027275

(51) Int. Cl.
*A61B 6/00* (2006.01)
*H02J 7/00* (2006.01)
*G05D 16/20* (2006.01)

(52) U.S. Cl.
CPC ............ *A61B 6/586* (2013.01); *A61B 6/4283* (2013.01); *A61B 6/4488* (2013.01); *A61B 6/54* (2013.01); *A61B 6/56* (2013.01); *G05D 16/2066* (2013.01); *H02J 7/0044* (2013.01)

(58) Field of Classification Search
CPC ..... A61B 6/586; A61B 6/4283; A61B 6/4488; A61B 6/54; A61B 6/56; G05D 16/2066; H02J 7/0044

USPC ......................................................... 378/103
See application file for complete search history.

(56) References Cited

U.S. PATENT DOCUMENTS

| D654,019 S | * | 2/2012 | Ikegame | ..................... D13/108 |
| D669,851 S | * | 10/2012 | Ikegame | ..................... D13/108 |
| 8,615,069 B2 | * | 12/2013 | Kamiya | ............... A61B 6/4233 378/102 |
| 9,675,314 B2 | | 6/2017 | Ota et al. | |
| 2010/0202586 A1 | * | 8/2010 | Nishino | ............... A61B 6/4283 378/62 |
| 2011/0280369 A1 | * | 11/2011 | Nishino | ............... A61B 6/4233 378/62 |

(Continued)

FOREIGN PATENT DOCUMENTS

JP 2016097036 A 5/2016

*Primary Examiner* — Taeho Jo
(74) *Attorney, Agent, or Firm* — Holtz, Holtz & Volek PC

(57) ABSTRACT

A radiographic imaging apparatus including a radiation detecting element that detects radiation with which a subject is irradiated and a casing that houses a battery, the casing being provided with a vent hole that circulates internal and external air, the radiographic imaging apparatus comprising: an air pressure measurer that measures an internal air pressure of the casing; a hardware processor that inspects, after the internal air pressure of the casing changes due to operation of pressure, waterproof performance of the radiographic imaging apparatus on a basis of a changing aspect of the internal air pressure due to termination of the operation of the pressure, and a flow rate regulator that reduces a flow rate of the air through the vent hole in a case where the battery is charged.

16 Claims, 14 Drawing Sheets

(56) References Cited

U.S. PATENT DOCUMENTS

| | | | | |
|---|---|---|---|---|
| 2012/0194132 A1* | 8/2012 | Ikegame | ............... | H02J 7/0045 320/113 |
| 2013/0003932 A1* | 1/2013 | Nishino | ............... | A61B 6/4283 378/91 |
| 2015/0222134 A1* | 8/2015 | Ikegame | ............... | H02J 7/0045 320/107 |
| 2015/0293239 A1* | 10/2015 | Miyoshi | .................... | G01T 7/00 250/394 |
| 2016/0143611 A1* | 5/2016 | Ota | ........................ | A61B 6/586 378/207 |
| 2017/0311920 A1* | 11/2017 | Hiroshige | ............ | A61B 6/4452 |

* cited by examiner

RADIOGRAPHIC IMAGING SYSTEM, RADIOGRAPHIC IMAGING APPARATUS, BATTERY CHARGER, AND METHOD OF INSPECTING WATERPROOF PERFORMANCE

CROSS REFERENCE TO RELATED APPLICATIONS

The entire disclosure of Japanese Patent Application No. 2018-27275 filed on Feb. 19, 2018 is incorporated herein by reference in its entirety.

BACKGROUND

Technological Field

The present invention relates to a radiographic imaging system, a radiographic imaging apparatus, a battery charger, and a method of inspecting waterproof performance.

Description of Related Art

There have been developed various radiographic imaging apparatuses that irradiate an affected part, that is, an imaging part of a patient with radiation such as an X-ray and capture an image of the radiation transmitted through the affected part. Most of conventional radiographic imaging apparatuses have been apparatuses of what is called a dedicated machine type or a fixed type integrally formed with a support table or the like. Meanwhile, in recent years, there has been developed a portable (also referred to as cassette type) radiographic imaging apparatus referred to as a flat panel detector (FPD), and has been put into practical use. The FPD has a configuration in which various electronic components including a radiation detecting element are housed in a casing, and is capable of generating charge using the detecting element according to a dose of the radiation with which the affected part is irradiated, generating image data on the basis of the generated charge, and outputting the generated image data to a computer for display.

In a similar manner to a computed radiography (CR) cassette that has been conventionally used for radiographic imaging (hereinafter simply referred to as imaging), such an FPD can be attached/detached to/from an imaging table at the time of imaging. In addition, the FPD has characteristics that are not found in the dedicated machine type apparatus, such as direct application to the patient's body and capability of being used in a state where the patient is placed on the FPD.

Incidentally, in a case where the FPD is applied to the patient's body or the imaging is performed in a state where the patient is placed on the FPD, body fluids (e.g., urine, blood, sweat, and saliva) of the patient may adhere to the FPD. Here, in a case where the adhered body fluid enters inside the casing of the FPD, in addition to sanitary problems being caused, various components inside the casing may be adversely affected, which may cause, for example, a failure of the FPD.

In recent years, in consideration of the usage state described above, FPDs of the type having a waterproof function in the casing have been widely used. Meanwhile, when the waterproof performance of the FPD (casing) is deteriorated due to durability and the like, the attached body fluid is likely to enter the inside of the FPD, which may cause the problem described above. Accordingly, it is necessary to regularly inspect the waterproof performance of the FPD.

As a method of inspecting the waterproof performance, Japanese Patent Application Laid-Open No. 2016-097036 discloses a technique in which responsiveness to a change in air pressure in the casing, which is caused by pressure to the casing and returns to the external atmospheric pressure, is measured and it is estimated whether and to what extent the waterproof performance is secured.

However, in the technique disclosed in Japanese Patent Application Laid-Open No. 2016-097036, it is not easy to cause a sufficient change in air pressure when the pressure is applied to the casing, whereby improvement has been required from the viewpoint of labor, skill, human resources, and the like necessary for inspecting the waterproof performance.

Specifically, the casing of the FPD is provided with a vent hole for keeping the internal and external atmospheric pressure constant. Meanwhile, according to the technique of Japanese Patent Application Laid-Open No. 2016-097036, when the waterproof performance is inspected, there is air that leaks (flows out) from the vent hole, whereby the waterproof performance cannot be accurately inspected in a short time. Moreover, according to the technique of Japanese Patent Application Laid-Open No. 2016-097036, while a user needs to manually close the vent hole to deal with this problem, a manner of closing the vent hole is different for each user, whereby it has also been difficult to secure the accuracy and quickness of the inspection of the waterproof performance.

SUMMARY

An object of the present invention is to provide a radiographic imaging system, a radiographic imaging apparatus, a battery charger, and a method of inspecting waterproof performance capable of quickly and accurately inspecting waterproof performance of the radiographic imaging apparatus in daily use.

To achieve at least one of the abovementioned objects, according to an aspect of the present invention, a radiographic imaging system reflecting one aspect of the present invention comprises:

a radiographic imaging apparatus including a radiation detecting element that detects radiation with which a subject is irradiated and a casing that houses a battery, the casing being provided with a vent hole that circulates internal and external air; and a battery charger to which the radiographic imaging apparatus is to be attached and which charges the battery, wherein the radiographic imaging apparatus includes an air pressure measurer that measures an internal air pressure of the casing, and a hardware processor that inspects, after the internal air pressure of the casing changes due to operation of pressure, waterproof performance of the radiographic imaging apparatus on a basis of a changing aspect of the internal air pressure due to termination of the operation of the pressure, and at least one of the radiographic imaging apparatus and the battery charger includes a flow rate regulator that reduces a flow rate of the air through the vent hole in a case where the radiographic imaging apparatus is attached to the battery charger.

To achieve at least one of the abovementioned objects, according to an aspect of the present invention, a radiographic imaging apparatus reflecting another aspect of the present invention is a radiographic imaging apparatus including a radiation detecting element that detects radiation with which a subject is irradiated and a casing that houses a battery, the casing being provided with a vent hole that circulates internal and external air, the radiographic imaging apparatus comprising:

an air pressure measurer that measures an internal air pressure of the casing;

a hardware processor that inspects, after the internal air pressure of the casing changes due to operation of pressure, waterproof performance of the radiographic imaging apparatus on a basis of a changing aspect of the internal air pressure due to termination of the operation of the pressure, and a flow rate regulator that reduces a flow rate of the air through the vent hole in a case where the battery is charged.

To achieve at least one of the abovementioned objects, according to an aspect of the present invention, a battery charger reflecting another aspect of the present invention is a battery charger provided in a radiographic imaging apparatus including a radiation detecting element that detects radiation with which a subject is irradiated and a casing that houses a battery, the casing being provided with a vent hole that circulates internal and external air, the battery charger charging the battery, the battery charger comprising:

a holder that holds the casing of the radiographic imaging apparatus; and a flow rate regulator that reduces a flow rate of the air through the vent hole in a state where the casing is held.

To achieve at least one of the abovementioned objects, according to an aspect of the present invention, a method of inspecting waterproof performance reflecting another aspect of the present invention is a method of inspecting waterproof performance that inspects waterproof performance of a radiographic imaging apparatus including a radiation detecting element that detects radiation with which a subject is irradiated and a casing that houses a battery, the casing being provided with a vent hole that circulates internal and external air, the method comprising:

operating, in a case where the battery is charged, internal air pressure of the casing in a state where a flow rate of the air through the vent hole is decreased by a flow rate regulator;

measuring the internal air pressure after operation; and inspecting the waterproof performance of the casing on a basis of a changing aspect of the measured internal air pressure.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Figure 1A:
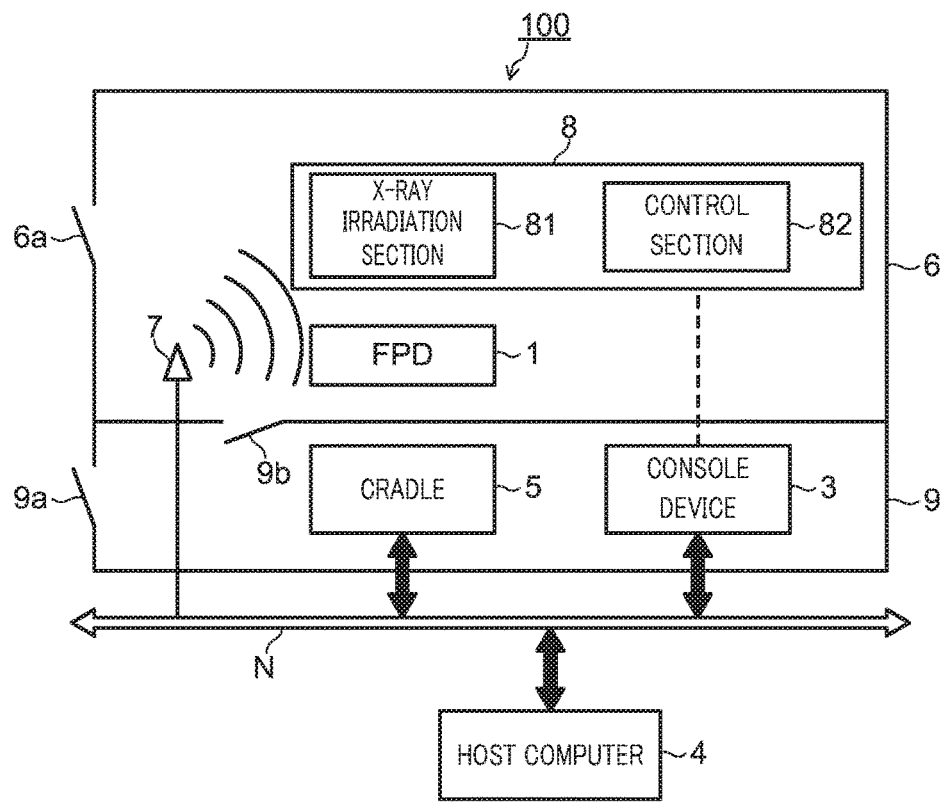
FIGS. 1A and 1B are schematic configuration diagrams of a radiographic imaging system according to the present embodiment.
Figure 1B:
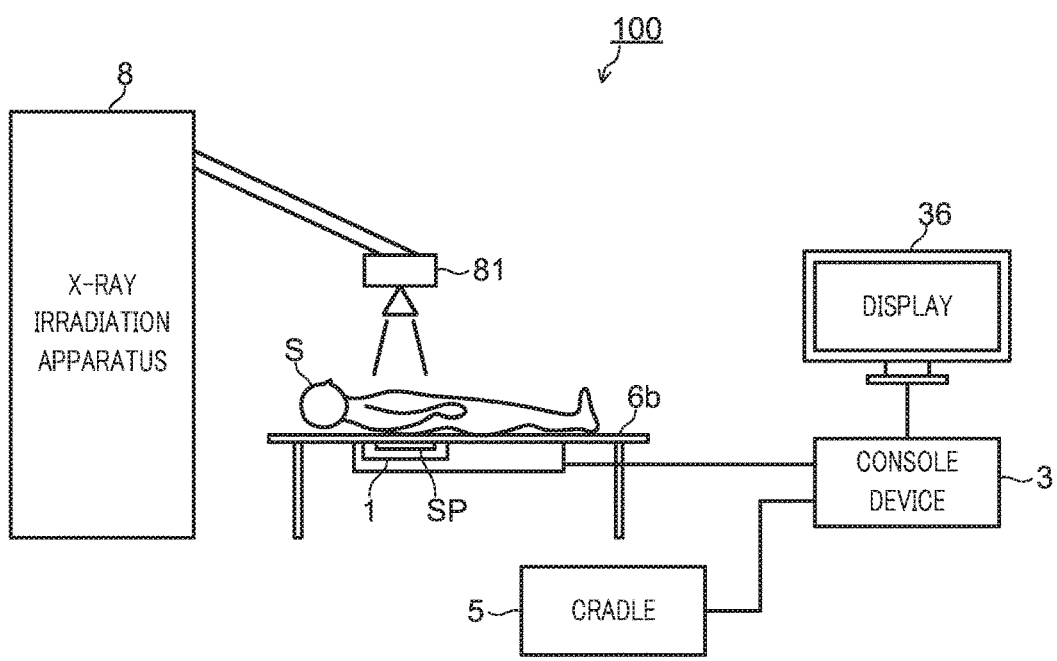

Hereinafter, an embodiment of a radiographic imaging system to which the present invention is applied will be described in detail with reference to the accompanying drawings. FIG. 1 (FIGS. 1A and 1B) illustrates a main configuration of X-ray imaging system 100 as a radiographic imaging system. X-ray imaging system 100 according to the present embodiment is a system that irradiates, in a hospital, a patient (hereinafter referred to as a subject) S with X-rays to capture an X-ray image (radiographic image).

X-ray imaging system 100 includes flat panel detector (FPD) 1 as a radiographic imaging apparatus that detects an X-ray (radiation) with which subject S is irradiated and outputs it as a radiographic image (captured image), and X-ray irradiation apparatus 8 that generates and emits the X-ray for irradiation. X-ray imaging system 100 further includes console device 3 that performs display and the like of the captured image output from FPD 1, cradle device (hereinafter simply referred to as a cradle) 5 as a peripheral device for charging a battery in FPD 1 and the like to be described later, and base station 7 for performing wireless communication between the above-described devices. Furthermore, X-ray imaging system 100 includes host computer 4 that performs, for example, management of various data in the hospital. The above-described devices included in X-ray imaging system 100 are connected to each other via network N.

In the example illustrated in FIG. 1, FPD 1, base station 7, and X-ray irradiation apparatus 8 are installed in, for example, imaging room 6 to which a measure to prevent radiation leakage to outside is applied using lead or the like. Meanwhile, console device 3 and cradle 5 are installed in front room 9 of imaging room 6. A user (doctor, etc.) and subject S can come and go between imaging room 6 and front room 9 through door 9b of front room 9, and can move to another hospital room or the like through door 6a of imaging room 6 and door 9a of front room 9. Host computer 4 is installed in a data management room (not illustrated) of the hospital.

X-ray irradiation apparatus 8 includes X-ray irradiation section 81 (see FIG. 1B) that includes a publicly known X-ray tube (vacuum tube) (not illustrated) and is used in a state being close to subject S, control section 82 that controls X-rays emitted from X-ray irradiation section 81, and the like. Control section 82 includes a power supply section that applies voltage to the X-ray tube of X-ray irradiation section 81, a processor that controls the power supply section, and the like. Among them, the power supply section includes a filament power supply for heating a filament provided at the cathode of the X-ray tube, and a high-voltage power supply for accelerating electrons to collide with a target on the anode surface of the X-ray tube. The processor controls the power supply of the filament power supply and the high-voltage power supply, thereby controlling X-rays emitted from the X-ray tube of X-ray irradiation section 81.

Console device 3 is a computer that provides instructions mainly on control of radiographic image capturing (hereinafter also simply referred to as X-ray imaging), display of the X-ray image obtained from FPD 1, details of image processing related to data of the X-ray image, and the like. Console device 3 includes a processor, an operation input section such as a mouse and a keyboard, and display 36 such as a liquid crystal display (LCD), and performs the above-described control, display, instructions, and the like through various screens such as a menu screen displayed on display 36.

Host computer 4 manages reservations of the X-ray imaging in the hospital, and when a reservation of the imaging is confirmed, it transmits an instruction of an imaging request (imaging order) to console device 3, and stores radiographic image data transferred from console device 3 after the X-ray imaging.

Figure 2:
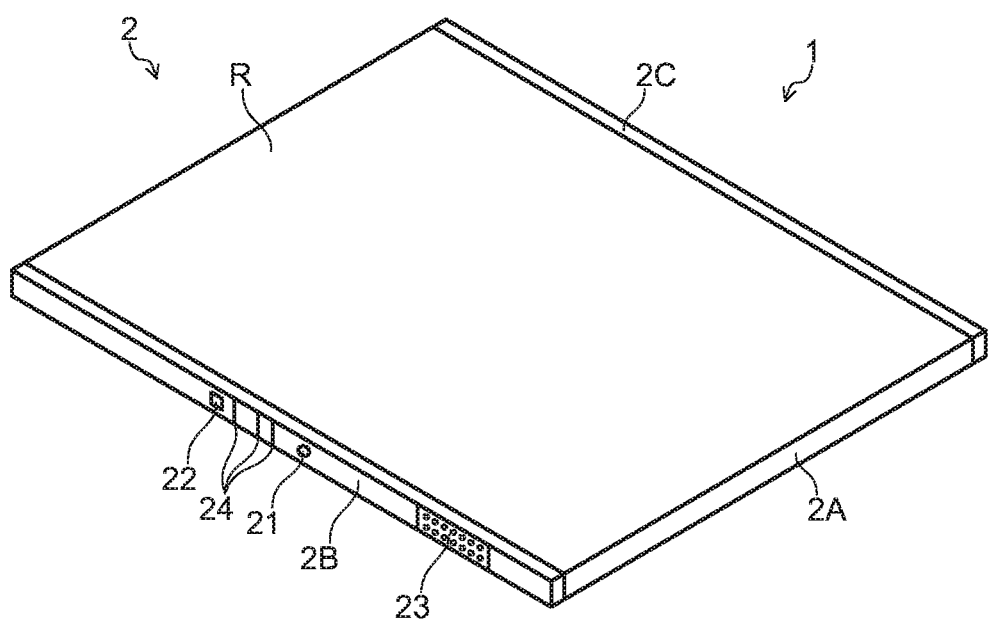
FIG. 2 is a perspective view illustrating an appearance of a radiographic imaging apparatus (FPD) according to the present embodiment.

FPD 1 houses, in casing 2 having a plate-like outer shape having a substantially rectangular planar shape illustrated in FIG. 2, sensor panel SP (see FIG. 1B) that detects X-rays. In the present embodiment, casing 2 includes hollow rectangular tubular housing main body 2A having X-ray incidence surface (exposure surface) R, and protective covers 2B and 2C that block openings on both sides of housing main body 2A. Housing main body 2A is formed of a carbon plate (i.e., carbon fibers hardened in a plate shape using resin or the like) that transmits radiation.

Note that the shape of casing 2 is not limited to the one described above, and may be any shape as long as it has a substantially rectangular planar shape such as a box shape. In a case where the shape of casing 2 is made in a box shape (i.e., in a case where housing main body 2A is formed in a shape of a container), materials other than the above-described carbon fibers and the like, for example, other materials such as a metal member, may be used as the material of back surface U (see FIG. 3) of housing main body 2A.

On protective cover 2B constituting a side surface of casing 2, power supply switch 21, changeover switch 22, connector 23, indicator 24, and the like are provided. Among them, connector 23 establishes electrical connection with an external device of FPD 1, which is connected to cradle 5 in the present embodiment. Further, indicator 24 includes a light emitting diode (LED) and the like, and has a function as a display for displaying a state of the battery to be described later, an operating state of FPD 1, and the like.

Although a detailed illustration is omitted, sensor panel SP of FPD 1 has a configuration in which a plurality of radiation detecting elements (photodiodes, etc.) is disposed in a two-dimensional matrix of n×m on a sensor substrate, and each of the radiation detecting elements detects the X-rays with which subject S is irradiated. In FIGS. 1B and 2, exposure surface R of casing 2 is illustrated on the upper side, and the radiation detecting element of sensor panel SP detects the X-rays transmitted through exposure surface R (hereinafter also referred to as surface R) of casing 2.

Further, FPD 1 includes a converter that converts the X-rays detected by the radiation detecting element into electric signals, an A/D converter that digitizes the converted electric signals, an output section that outputs the digitized signals to console device 3 as a captured image, and the like. Other configurations of FPD 1 will be described later.

Cradle 5 functions as a peripheral device or an attachment device of FPD 1. In the present embodiment, cradle 5 functions as a battery charger for charging the battery of FPD 1 to be described later, and includes a power supplying section that supplies power (charging current) to FPD 1, a processor that controls the power supplying section and cradle 5 in their entirety, and the like.

Figure 3:
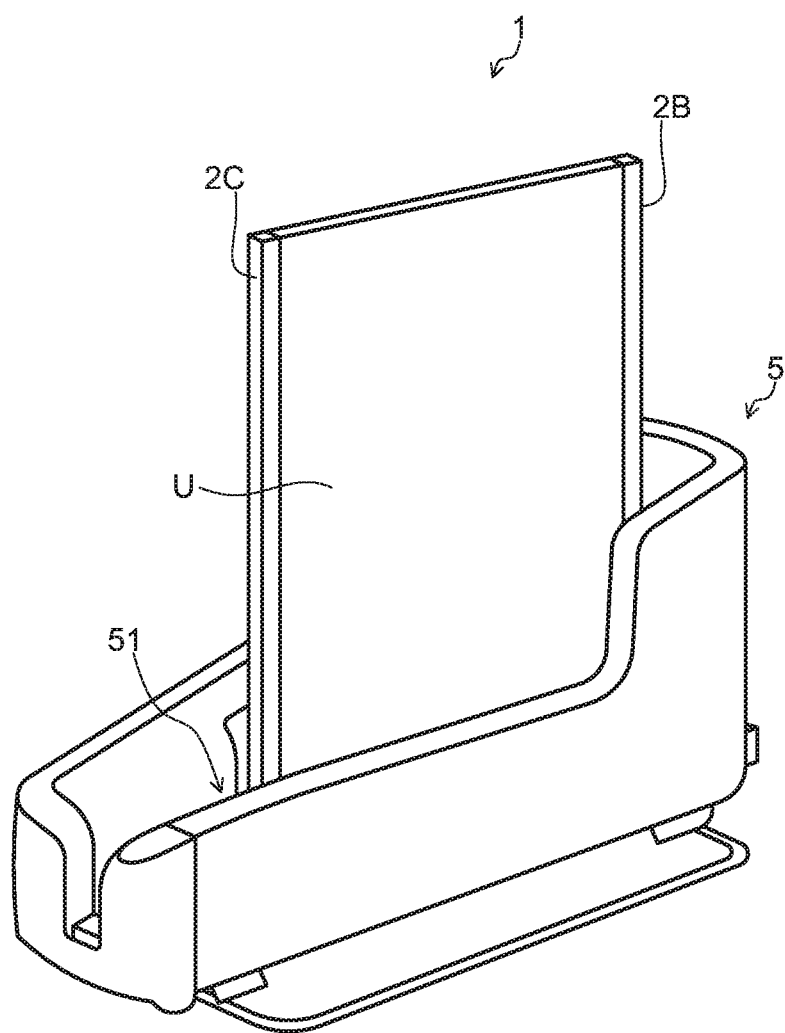
FIG. 3 is an external view illustrating a state in which the FPD is attached to a cradle.

As illustrated in FIG. 3, cradle 5 can attach FPD 1 at the time of charging the battery of FPD 1 or the time at which the X-ray imaging is not performed. Accordingly, there is provided holder 51 into which FPD 1 is inserted and held therein in the casing of cradle 5. FIG. 3 illustrates a state in which back surface U of casing 2 to be a non-exposure surface is set on the front side and FPD 1 is attached to holder 51 of cradle 5 with protective covers 2B and 2C being set on the right side and the left side, respectively. In this attached state, connector 23 of protective cover 2B as described above is connected to a charging connector (not illustrated) provided at a corresponding position of holder 51, and the battery of FPD 1 is charged by cradle 5.

Hereinafter, schematic operation of X-ray imaging system 100 will be described with an example of performing X-ray imaging on the chest of subject S.

Prior to this X-ray imaging, a menu screen (not illustrated) is displayed on display 36 of console device 3. In the present embodiment, according to operation of a mouse of console device 3 or the like, a patient database is accessed from the menu screen, various kinds of information (patient ID, name, birth date, gender, name of the affected part to be imaged (in this example, front chest), etc.) associated with the patient to be subject S (hereinafter simply referred to as subject S) is input in advance, thereby registering and updating the patient database.

Further, prior to the X-ray imaging, the position of FPD 1 attached to decubitus table 6b is adjusted to be the position of the chest of subject S. Subsequently, subject S is laid in a supine position on decubitus table 6b, position adjustment is performed such that the back of subject S is located at the position corresponding to FPD 1, and X-ray irradiation section 81 is moved to the position facing the front chest of the patient.

Furthermore, an operation screen (not illustrated) for executing the X-ray imaging is displayed on display 36 through the menu screen, and a parameter such as intensity of X-rays emitted from X-ray irradiation section 81 is input by input operation of the mouse of console device 3 or the like through the operation screen. Subsequently, when an imaging button (not illustrated) displayed on the operation screen is selected, X-ray irradiation apparatus 8 operates, and X-rays are emitted from X-ray irradiation section 81 according to the set parameter.

The emitted X-rays are transmitted through the affected part of subject S, and sensor panel SP of FPD 1 is irradiated with the X-rays. FPD 1 detects the intensity (strength distribution) of the X-rays transmitted through the affected part of subject S using sensor panel SP, converts the detected X-rays into electric signals, and digitizes the converted electric signals, thereby generating a captured image. The generated captured image data is then transferred from FPD1 to console device 3, and is displayed on display 36 as an X-ray image. This X-ray image is processed by console device 3 as appropriate, transferred to host computer 4, and stored in the patient database or the like included in host computer 4.

Incidentally, in a case where FPD 1 is applied to the body of subject S or the imaging is performed in a state where subject S is placed on the FPD, body fluids (e.g., urine, blood, sweat, and saliva) of subject S may adhere to FPD 1. Here, in a case where the adhered body fluid enters inside casing 2 of FPD 1, in addition to sanitary problems being caused, various components inside casing 2 may be adversely affected, which may cause, for example, a failure of FPD 1.

In consideration of the usage state described above, as will be described later with reference to FIG. 4, casing 2 of FPD 1 according to the present embodiment has a structure including a waterproof function that prevents, while ensuring breathability of casing 2, fluid from entering the inside of casing 2. Meanwhile, when the waterproof performance of FPD 1 (casing 2) is deteriorated due to the durability and the like, the attached body fluid is likely to enter the inside of FPD 1, which may cause the problem described above. Accordingly, it is necessary to regularly inspect the waterproof performance of FPD 1.

Hereinafter, the configuration of casing 2 of FPD 1 will be described in more detail with reference to FIG. 4. Casing 2 of FPD 1 is provided with vent hole H through which the internal and external air of casing 2 can circulate. This vent hole H functions such that, when FPD 1 is transported by air or is used at a place of a high altitude, a malfunction due to air pressure inside casing 2 becoming higher than the external atmospheric pressure and casing 2 being expanded (e.g., damage of sensor panel SP) is reduced. FIG. 4 illustrates an example in which a vent hole H is provided in the side surface of casing 2 to which protective covers 2B and 2C are attached. Note that vent hole H can be formed in various positions such as a portion in back surface U (see FIG. 3) of housing main body 2A of casing 2, a peripheral portion of surface R, and any side surface of housing main body 2A. In addition, the shape, size, number, and the like of vent hole H can be optional. A plurality of vent holes H can be provided in casing 2 in consideration of heat radiation of electronic components inside FPD 1 and the like.

Figure 4:
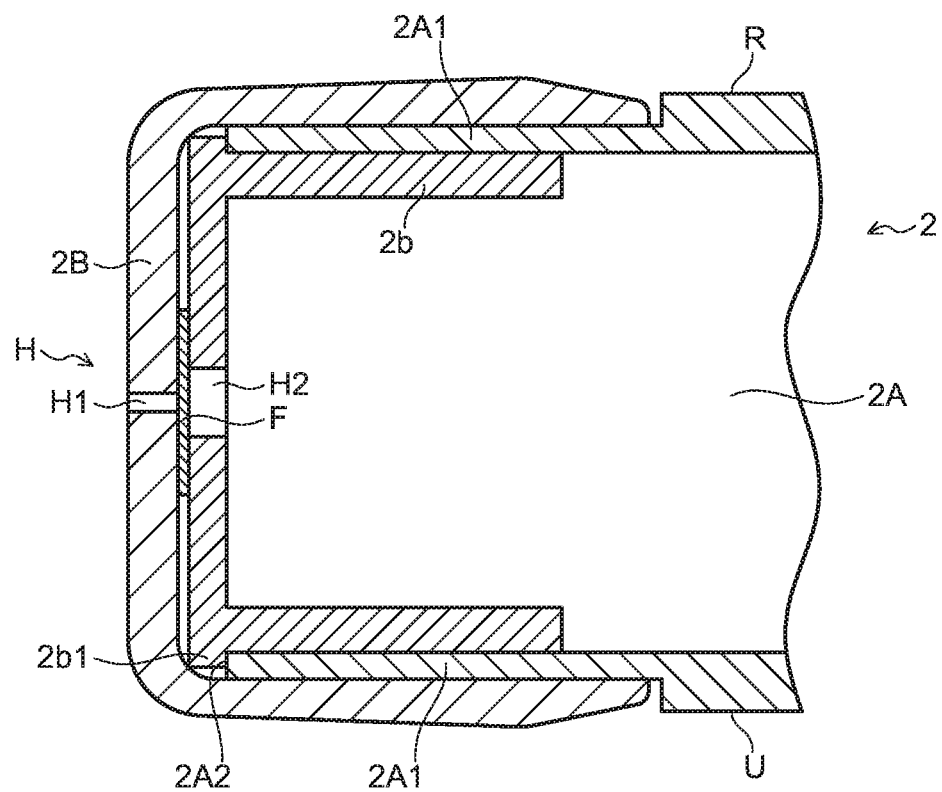
FIG. 4 is a cross-sectional view illustrating an exemplary configuration around a vent hole of the FPD.

In the example illustrated in FIG. 4, inner cover 2b is inserted inside end portion 2A1 of housing main body 2A of casing 2, and locking portion 2b1 of inner cover 2b is locked to tip 2A2 of end portion 2A1, whereby the opening of housing main body 2A is sealed by inner cover 2b. In addition, protective cover 2B is attached to cover end portion 2A1 of housing main body 2A and the outside of inner cover 2b, whereby the opening of housing main body 2A is blocked. The side of protective cover 2C is similarly configured.

Further, in the example illustrated in FIG. 4, holes H1 and H2 are bored in protective cover 2B and inner cover 2b, respectively, and holes H1 and H2 are provided at the positions that communicate with each other, whereby vent hole H is formed in the side surface of casing 2 of FPD 1. Furthermore, water-shedding ventilation filter F is provided in vent hole H to suppress infiltration of fluid into casing 2 through vent hole H and to enable ventilation.

According to such a configuration, circulation of the internal and external air of casing 2 is performed through vent hole H formed by holes H1 and H2 provided in protective cover 2B and inner cover 2b, respectively, and through ventilation filter F. Meanwhile, even when body fluid of subject S or the like enters vent hole H (hole H1 of protective cover 2B), such body fluid or the like is shed by water-shedding ventilation filter F, whereby infiltration of fluid or the like into casing 2 from vent hole H can be suppressed.

As ventilation filter F, for example, a fluororesin-based film such as a polytetrafluoroethylene (PTFE) porous film can be used, and films made of other materials having breathability may be used as long as the above-described function is secured.

Meanwhile, for the components such as power supply switch 21, changeover switch 22, connector 23, and indicator 24 described with reference to FIG. 2, a waterproof packing using a seal material such as rubber is disposed at the place for attaching the components (in this example, protective cover 2B).

Note that, in a case where casing 2 is box-shaped as a variation, that is, in a case where housing main body 2A is formed in a shape of a container, only one of the above-described protective covers 2B and 2C may be used as a cover part and the other one may be omitted. In this case, the above-described waterproof packing may be disposed between the protective cover (2B or 2C) used as the cover part and the place for attaching housing main body 2A.

According to such a configuration, casing 2 of FPD 1 has a structure having waterproof performance for suppressing infiltration of fluid into casing 2. Meanwhile, since FPD 1 is easily carried, it may hit or fall on a floor while being moved. In this case, due to the impact (external force) applied to FPD 1, for example, the gap between end portion 2A1 of housing main body 2A and protective covers 2B and 2C may be enlarged, or a minute crack or the like may occur in those components, which may result in deterioration in waterproof performance. Even in a normal usage state, due to a long-term use, the above-described waterproof packing and each part of casing 2 are deteriorated, and the original waterproof performance of casing 2 is gradually deteriorated. Therefore, the waterproof performance of FPD 1 needs to be inspected regularly.

With respect to the inspection of the waterproof performance, in the technique disclosed in Japanese Patent Application Laid-Open No. 2016-097036, it is not easy to cause a sufficient change in air pressure when the pressure is applied to casing 2, whereby improvement has been required from the viewpoint of labor, skill, human resources, and the like necessary for inspecting the waterproof performance.

More specifically, in the technique disclosed in Japanese Patent Application Laid-Open No. 2016-097036, the air flows out from vent hole H through ventilation filter F, whereby it has not been easy to achieve, in a short time, the sufficient change amount of the internal air pressure of casing 2 necessary for starting the waterproof performance inspection. Moreover, in the technique disclosed in Japanese Patent Application Laid-Open No. 2016-097036, there has been a problem that, due to the air leaking (outflowing) from vent hole H at the time of inspecting the waterproof performance, an air leakage amount to be truly determined (change amount of the internal air pressure) is made unclear due to the air leakage amount flown out through vent hole H. Therefore, according to the technique disclosed in Japanese Patent Application Laid-Open No. 2016-097036, it has been difficult to accurately inspect the waterproof performance of FPD 1 in a short time.

According to the technique disclosed in Japanese Patent Application Laid-Open No. 2016-097036, while the user needs to, in order to deal with the problem described above, manually close vent hole H at the time of inspecting the waterproof performance, there has been a limit to securing labor, skill, human resources, and the like in a medical site such as a hospital. In addition, when vent hole H is manually closed, depending on the configuration of vent hole H (number, arrangement, shape, etc.), it is difficult to sufficiently close vent hole H, or the manner of closing vent hole H differs depending on the user, whereby it has been difficult to secure the quickness and accuracy of the inspection. From another point of view, according to the technique disclosed in Japanese Patent Application Laid-Open No. 2016-097036, there has been a problem that flexibility of the design with respect to the configuration of vent hole H (number, arrangement, shape, etc.) is substantially limited.

In view of the problems described above, in the present embodiment, in order to secure the sufficient change amount (deviation from the atmospheric pressure) of the internal air pressure of casing 2 necessary for starting the waterproof performance inspection, a flow rate regulator that reduces the flow rate of the air through vent hole H is provided so that the internal air pressure of casing 2 reaches the peak value. Here, the flow rate regulator may be provided in either one of or both of FPD 1 and cradle 5 (peripheral device). Hereinafter, an exemplary configuration in which the flow rate regulator is provided in FPD 1 will be described.

Figure 5:
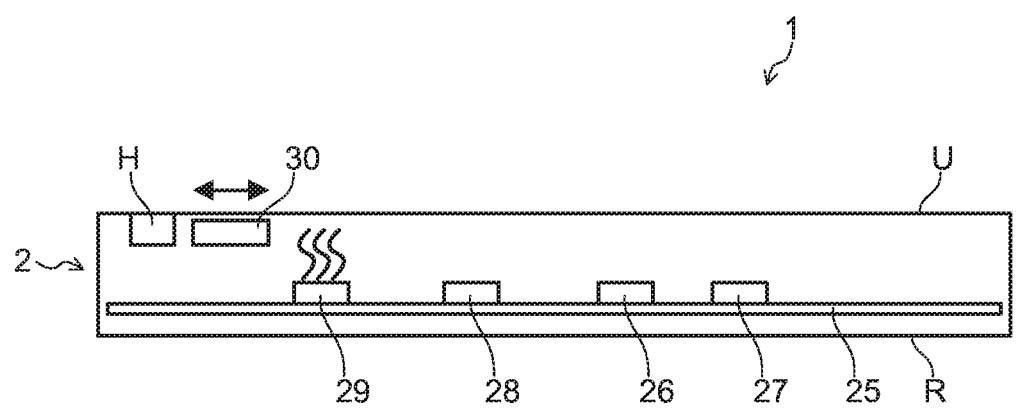
FIG. 5 is a schematic configuration diagram for illustrating a main part of the FPD according to the present embodiment.

Next, a configuration of FPD 1 and the like with respect to the flow rate regulator and the waterproof performance inspection will be described with reference to FIG. 5 and the subsequent drawings. FIG. 5 is a diagram schematically illustrating components inside casing 2 of FPD 1 according the present embodiment, and illustration of the battery, sensor panel SP, and the like is omitted for simplicity.

As illustrated in FIG. 5, circuit board 25 is housed in casing 2 of FPD 1, and on circuit board 25, there are mounted CPU 26 that controls each section, memory 27 as an external storage device of CPU 26, air pressure sensor 28 that detects the air pressure inside casing 2, heat source 29, and the like.

CPU 26 controls each section of FPD 1, communicates with an external device, and executes various processes related to the waterproof performance inspection to be described later.

Memory 27 includes various data storage media such as a RAM, an HDD, and a flash memory, and stores various programs including a waterproof performance inspection program read and executed by CPU 26, characteristic data of FPD 1 having normal waterproof performance to be described later, and the like.

Air pressure sensor 28 has a membrane structure inside thereof, and measures film displacement caused by the pressure difference between both sides of the film, thereby measuring the air pressure (hereinafter referred to as internal air pressure) inside casing 2. Air pressure sensor 28 functions as an air pressure measurer that measures the internal air pressure of casing 2.

In the embodiment illustrated in FIG. 5, unlike the example illustrated in FIG. 4, vent hole H is provided at a position close to back surface U of casing 2. Further, in the present embodiment, shutter 30 as an opening degree control member for adjusting an opening degree of vent hole H is provided to be movable within casing 2. In this example, shutter 30 is connected to a driving source such as a motor and a solenoid (not illustrated), and the driving source is driven under the control of CPU 26, whereby shutter 30 moves in the direction indicated by the double-headed arrow in FIG. 5.

FIG. 5 illustrates a state in which vent hole H is fully opened. When shutter 30 moves, from this state, in the left direction in the drawing under the control of CPU 26, the inner side of vent hole H (see hole H2 in FIG. 4) is covered with shutter 30, and the air flow through vent hole H is prevented or substantially suppressed, thereby improving airtightness of casing 2. Therefore, CPU 26 functions as a position controller for controlling the position of shutter 30 with respect to vent hole H. Further, in this example, shutter 30, the driving source thereof, and CPU 26 constitute the flow rate regulator that regulates the flow rate of the air through vent hole H.

Although illustration is omitted, a battery (power supply battery) for supplying current to each section of FPD 1 described above is housed in casing 2. Examples of this battery include a rechargeable battery capable of being repeatedly charged such as a lithium ion battery. Sensor panel SP described above can be disposed between circuit board 25 and casing 2, or can be disposed on the lower surface of circuit board 25.

Heat source 29 is one or more electronic components that generate heat at the time of the waterproof performance inspection (at the time of charging the battery, at the time of operating air pressure sensor 28, etc.) to be described later, which includes various items housed in casing 2. Examples of heat source 29 include a coil of a power supply circuit used at the time of charging, a readout integrated circuit (ROIC), and a wireless module for performing wireless communication with other devices in X-ray imaging system 100. In addition, heat source 29 can include various kinds of electronic components (heater, etc.).

In this example, CPU 26 and heat source 29 function as an air pressure operation section for operating the internal air pressure of casing 2 (i.e., for causing a change from the atmospheric pressure).

In general, the Boyle-Charles' law can be applied in a space where the airtightness is kept to a certain extent, and a proportional relationship is established between the temperature and the pressure of the air. In the present embodiment, the temperature of the air inside casing 2 is operated (heating is performed, and heating is stopped) using this principle, thereby operating (pressurizing and depressurizing) the air pressure inside casing 2.

Figure 6A:
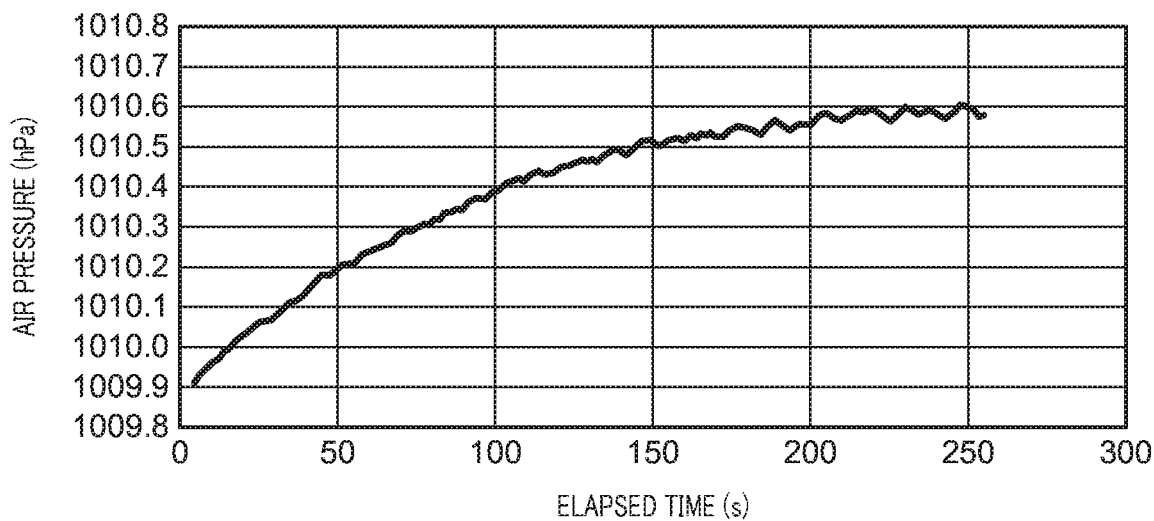
FIGS. 6A and 6B are characteristic graphs illustrating actual measurement results of internal air pressure during charging of a battery and after the charging in the FPD.
Figure 6B:
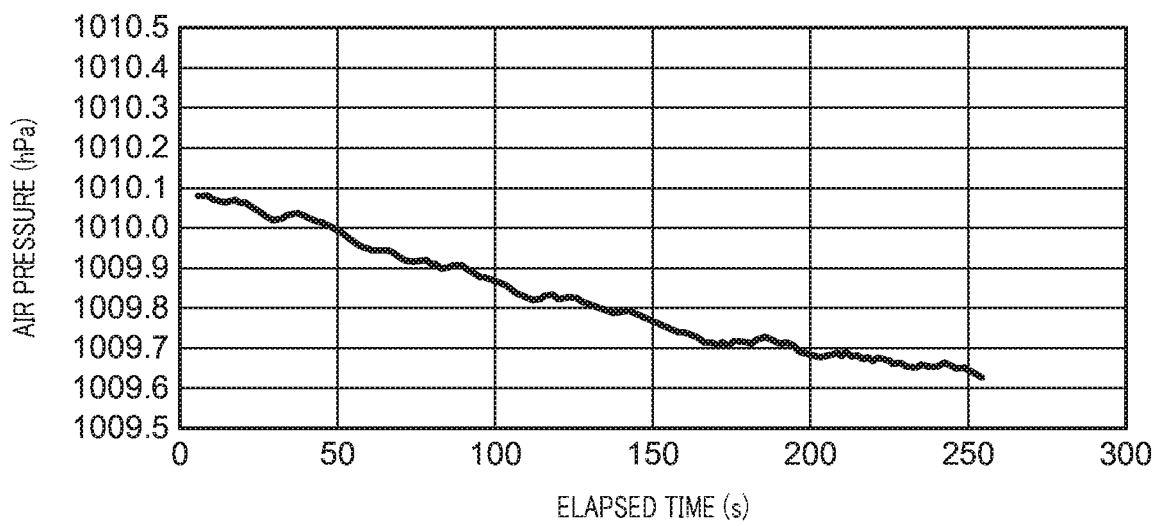

FIGS. 6A and 6B are characteristic graphs illustrating actual measurement results of the internal air pressure of FPD 1 during charging of the battery in FPD 1 having normal waterproof performance of casing 2 using cradle 5 and after the charging is complete. At the time of such actual measurement, the internal air pressure of FPD 1 has been measured in such a manner that the position of shutter 30 is moved from the state illustrated in FIG. 5 to the left side to close vent hole H in advance so that casing 2 is made substantially airtight.

Accordingly, as can be understood from FIG. 6A, the temperature of heat source 29 increases and the air inside casing 2 is warmed during the charging of the battery, whereby the internal air pressure of FPD 1 gradually increases according to the Boyle-Charles' law. After the charging of the battery is complete, no power is supplied to the battery and heat source 29, and the temperature of the air inside casing 2 gradually decreases to be equal to the external temperature as the temperature of heat source 29 decreases. Therefore, after the charging of the battery is complete, the internal temperature decreases, whereby the internal air pressure inside casing 2 gradually decreases toward the atmospheric pressure as illustrated in FIG. 6B.

Figure 7:
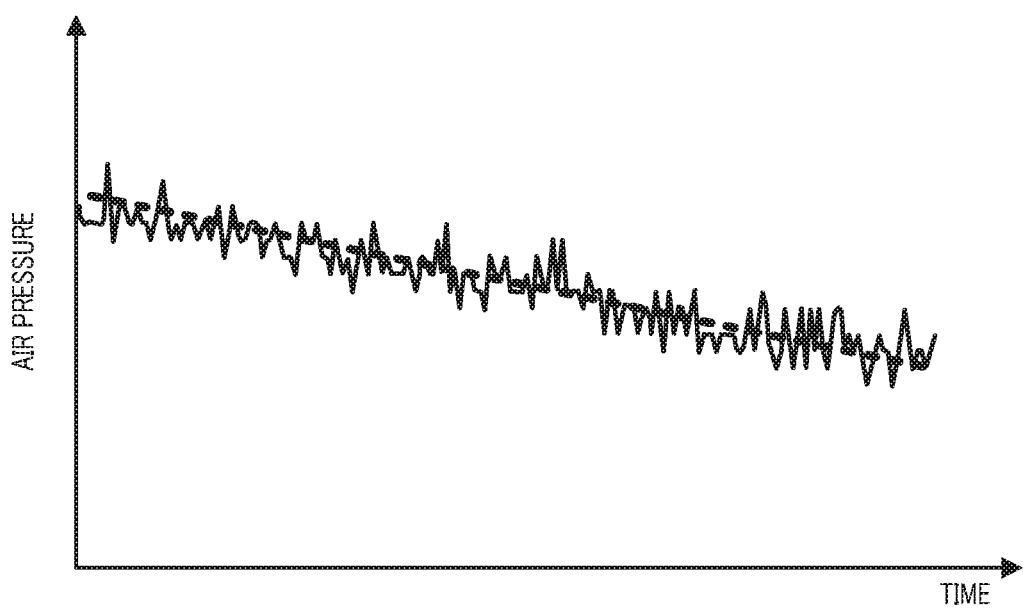
FIG. 7 is a graph illustrating processing of correcting a value detected by an air pressure sensor.

Note that the actual measured value (raw data of the output waveform) obtained by air pressure sensor 28 has minute variations of about ±0.1 hpa as illustrated by the solid line in FIG. 7. Therefore, at the time of measuring the internal air pressure of FPD 1, CPU 26 preferably corrects the minute variations of the measured values (raw data) obtained by air pressure sensor 28 such that the variations are averaged as indicated by the dotted line in FIG. 7. By performing such correction processing, the evaluation accuracy of the waterproof performance can be improved. As will be described later, in a case where the measured value of the air pressure change of FPD 1 having normal waterproof performance of casing 2 is used as an object to be compared with, the data after the above-described correction is performed is preferably stored in memory 27 or the like.

Figure 8:
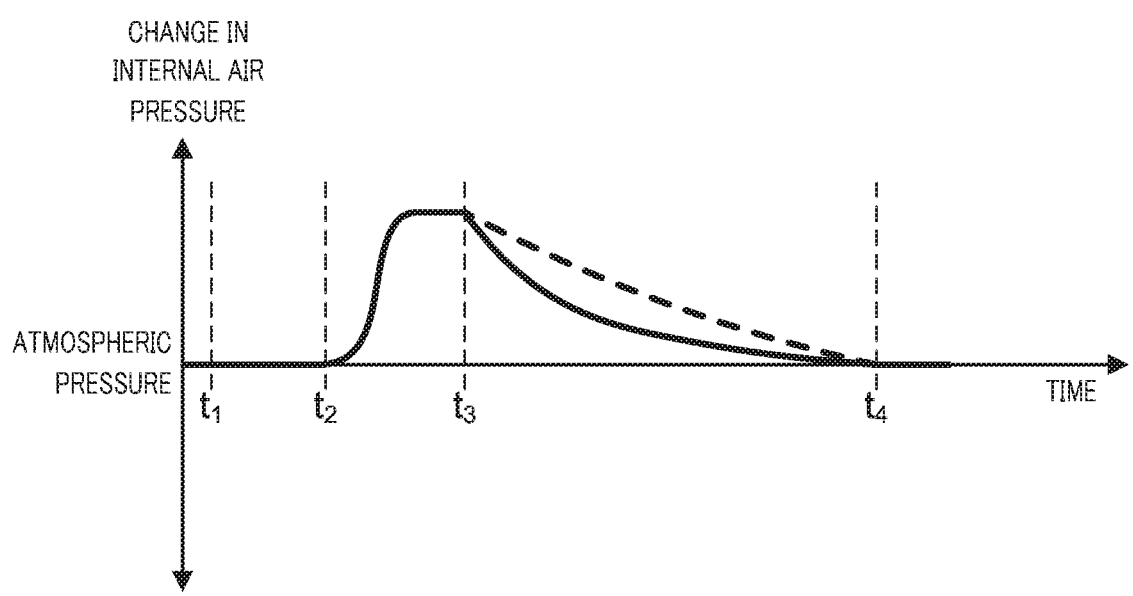
FIG. 8 is a characteristic graph illustrating a method of measuring a change in internal air pressure of the FPD according to the present embodiment.

Next, the method of inspecting the waterproof performance of FPD 1 (casing 2) will be described more specifically. FIG. 8 is a characteristic graph exemplifying how the internal air pressure of casing 2 changes. The vertical axis represents the value of the internal air pressure of casing 2, and the horizontal axis represents the passage of time (t).

In the present embodiment, under the control of CPU 26, shutter 30 is moved to lower the opening degree of vent hole H during the period from time $t_1$ at which FPD 1 is attached to cradle 5 to time $t_2$ at which the pressurization is started. By this processing, the airtightness of casing 2 having normal waterproof performance is secured, and the airtightness of casing 2 having deteriorated waterproof performance is lowered according to the degree of the deterioration.

Then, CPU 26 starts processing of air pressure operation (in this example, pressurization) that changes (in this example, increases) the air pressure inside casing 2 from time $t_2$ after the opening degree of vent hole H is lowered by the movement of shutter 30, and terminates the processing of the air pressure operation at time $t_3$ after the internal air pressure reaches the peak value.

In the present embodiment, as described above, the rise in air pressure caused by heat source 29 generating heat at the time of charging the battery in FPD 1 and the air inside casing 2 being warmed (the temperature rises) is utilized as the processing of the air pressure operation (see FIG. 6A). At this time, additional or supplementary processing of the air pressure operation (pressurization) to be described later may be performed.

In this manner, when the pressurizing operation inside casing 2 is complete, the internal air pressure of FPD 1 gradually fluctuates (in this case, decreases) to be equal to the atmospheric pressure (see FIG. 6B). Accordingly, CPU 26 measures the manner of variation (lowering) of the air pressure from time $t_3$ at which the air pressure operation is terminated until time $t_4$ at which the air pressure returns to the atmospheric pressure. Here, during the period from time $t_3$ to $t_4$ in FIG. 8, the manner of changing the internal air pressure of FPD 1 having the normal waterproof performance is indicated by the bold dotted line, and the manner of changing the internal air pressure of FPD 1 having the deteriorated waterproof performance is indicated by the solid line. As can be understood by comparing those two curves, in the case of FPD 1 having the normal waterproof performance, the manner of changing (decreasing) the internal air pressure until the air pressure returns to the atmospheric pressure from the peak value is gradual in its entirety. On the other hand, in the case of FPD 1 having the deteriorated waterproof performance, the pressurized air inside casing 2 leaks from the deteriorated portion to the outside, whereby the manner of changing (inclination of lowering) the internal air pressure from the peak value is larger.

Note that, in FIG. 8, for clarification, only the characteristics of the air pressure variation during the period between times $t_3$ and $t_4$ differ in the case of FPD 1 having the normal waterproof performance and in the case of FPD 1 having the deteriorated waterproof performance. In practice, the characteristics of the air pressure variation during the period between times $t_2$ and $t_3$ may differ in the case of the normal waterproof performance and in the case of the deteriorated waterproof performance. However, since the characteristics of the air pressure variation during the period between times $t_2$ and $t_3$ vary depending on factors other than the waterproof performance (e.g., charging environment such as the remaining amount of the battery), it is difficult to obtain certain characteristics regardless of the waterproof performance (normal or deteriorated). Moreover, as will be described later, various modifications are conceivable for the processing of the air pressure operation for changing the internal air pressure of casing 2 to the peak value, and the characteristics of the air pressure variation during the period between times $t_2$ and $t_3$ change depending on the contents of such processing.

Meanwhile, during the period between time $t_3$ at which the air pressure operation is terminated (time at which the internal air pressure reaches the peak) and time $t_4$ at which the air pressure returns to the atmospheric pressure, the characteristics of the air pressure variation is entirely based on the airtightness of casing 2, whereby the manner of variation (lowering) of the internal air pressure can be easily distinguished between the case of the normal waterproof performance and the case of the deteriorated waterproof performance. Therefore, in the present embodiment, the waterproof performance of FPD 1 is basically evaluated from the manner of the air pressure variation (characteristics, feature point, etc.) during the above-described period between times $t_3$ and $t_4$, which is measured by air pressure sensor 28.

In the present embodiment, CPU 26 extracts the feature amount of the change in the internal air pressure of casing 2 during the period between time $t_3$ at which the air pressure operation is terminated and time $t_4$ at which the air pressure reaches the atmospheric pressure, thereby estimating a deterioration degree of the waterproof performance of FPD 1. Hereinafter, such a method will be described with reference to FIGS. 9 and 10.

Figure 9:
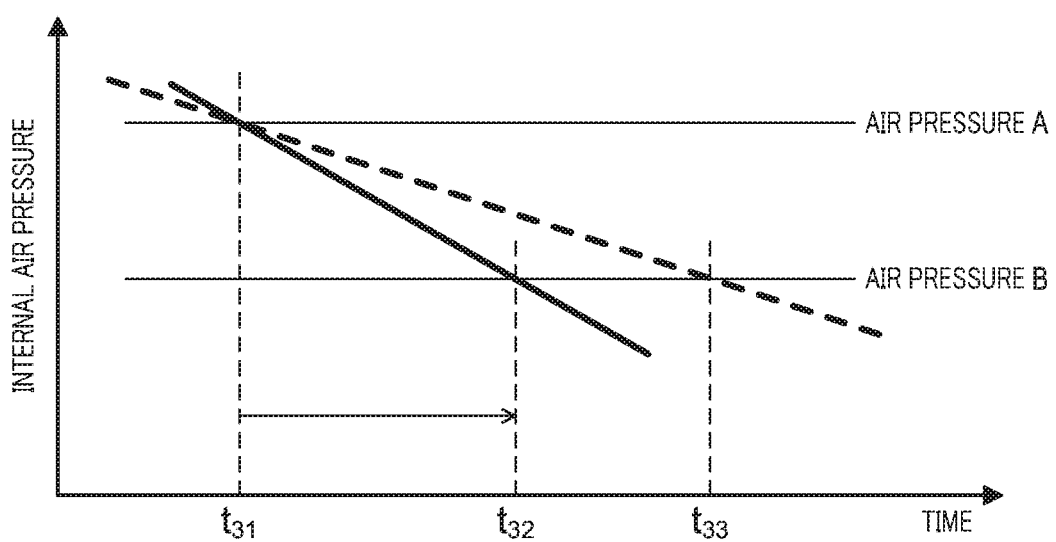
FIG. 9 is a characteristic graph illustrating a method of extracting a feature amount at the time of measuring the internal air pressure of the FPD.
Figure 10:
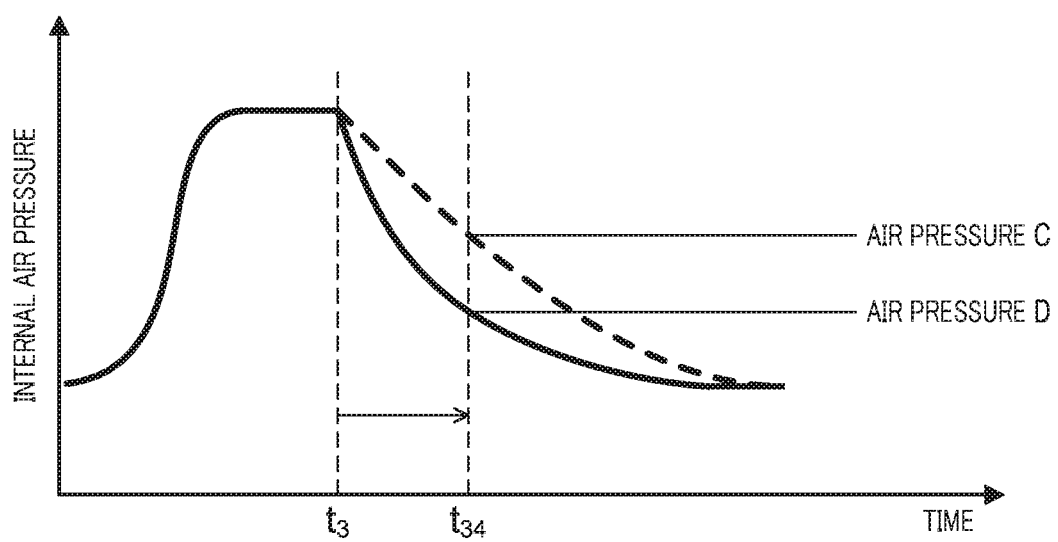
FIG. 10 is another characteristic graph illustrating the method of extracting the feature amount at the time of measuring the internal air pressure of the FPD.

FIGS. 9 and 10 illustrate specific examples of the method of extracting the feature amount of the manner of decreasing the internal air pressure after the internal air pressure of FPD 1 is raised to the peak value. In FIGS. 9 and 10, the change characteristic of the internal air pressure of FPD 1 having the deteriorated waterproof performance is indicated by the solid line, and the change characteristic of the internal air pressure of FPD 1 having the normal waterproof performance is indicated by the dotted line.

As illustrated in FIG. 8, the inclination of the air pressure change with respect to FPD 1 having the deteriorated waterproof performance is, compared with FPD 1 having the normal waterproof performance, basically large during the period from the time point (time $t_3$) at which the air pressure operation is terminated to a predetermined time point (i.e., time point at which the internal air pressure decreases to a certain extent). Therefore, within this range, estimation of a degree of the waterproof performance deterioration, determination of superiority/inferiority, and the like are easily performed. On the other hand, the inclination of the air pressure change from a time point at which the internal air pressure decreases to a certain extent to the time point at which the air pressure returns to the atmospheric pressure is difficult to distinguish between FPD 1 having the deteriorated waterproof performance and FPD 1 having the normal waterproof performance in some cases. Furthermore, the length of time from time $t_3$ to $t_4$ at which the air pressure returns to the atmospheric pressure may be different between FPD 1 having the normal waterproof performance and FPD 1 having the deteriorated waterproof performance, and in general, the larger the deterioration degree of the waterproof performance becomes, the shorter the time required for returning to the atmospheric pressure (from time $t_3$ to $t_4$) becomes. In general, it is preferable that the estimation of the degree of the waterproof performance deterioration, the determination of the superiority/inferiority, and the like are performed by CPU 26 promptly from the time point at which the air pressure operation is terminated (time $t_3$), and have already been terminated at a time point when the internal air pressure of FPD 1 approaches to the atmospheric pressure to a certain extent.

In view of the above, in the present embodiment, as illustrated in FIGS. 9 and 10, CPU 26 basically performs the estimation of the degree of the waterproof performance deterioration, the determination of the superiority/inferiority, and the like in the region where the inclination of the air pressure change of FPD 1 having the deteriorated waterproof performance is larger than that of FPD 1 having the normal waterproof performance.

More specifically, as illustrated in FIG. 9, CPU 26 calculates the time or the inclination of the air pressure change (air pressure variation value/time) from the time ($t_{31}$) at which the internal air pressure of FPD 1 is the peak value or air pressure A slightly lower than the peak value to the time at which the air pressure decreases to air pressure B. Note that air pressure B is lower than air pressure A, and is considerably higher than the atmospheric pressure.

Here, the length of time from the time at which the air pressure becomes air pressure A ($t_{31}$) to the time at which the air pressure decreases to air pressure B ($t_{32}$) is shorter in the case of FPD 1 having the deteriorated waterproof performance than in the case of FPD 1 having the normal waterproof performance (time from $t_{31}$ to $t_{33}$). Further, the inclination of the air pressure change from the time point at which the air pressure becomes air pressure A ($t_{31}$) to the time point at which the air pressure decreases to air pressure B ($t_{32}$) is larger in the case of FPD 1 having the deteriorated waterproof performance than in the case of FPD 1 having the normal waterproof performance. Furthermore, as the degree of the waterproof performance deterioration of casing 2 increases, the time required for FPD 1 to decrease from air pressure A to air pressure B becomes short, and the inclination of the air pressure change increases.

Therefore, CPU 26 calculates, from the detection result of air pressure sensor 28, the time required for the internal air pressure of FPD 1, which is the target of the waterproof performance inspection, to decrease from air pressure A to air pressure B or the inclination of the air pressure change as the feature amount. Then, CPU 26 compares the calculates time or the inclination of the air pressure change with the time or the inclination of the air pressure change in the case of FPD 1 having the normal waterproof performance, whereby the degree of the waterproof performance deterioration of FPD 1 to be inspected can be estimated. Here, the characteristics of FPD 1 having the normal waterproof performance (time required for air pressure A to decrease to air pressure B, or inclination of the air pressure change) are stored in memory 27 in such a manner that actual values measured under the same conditions such as the opening degree of vent hole H and the peak value are set as a table, which are read by CPU 26 at the time of inspecting the waterproof performance.

Another exemplary method of evaluating the waterproof performance of FPD 1 will be described with reference to FIG. 10. As described above, in the case of FPD 1 having the deteriorated waterproof performance, the pressurized air inside casing 2 leaks from the deteriorated portion to the outside, whereby the manner of changing (inclination of lowering) the internal air pressure from the peak value is larger. Meanwhile, when the pressurized air in casing 2 leaks to a certain extent, the manner of changing (inclination of lowering) the air pressure becomes relatively moderate thereafter.

In consideration of the phenomenon described above, as illustrated in FIG. 10, it is assumed that there is time or a period of time at which the air pressure difference between the internal air pressure of FPD 1 having the normal waterproof performance and the internal air pressure of FPD 1 having the deteriorated waterproof performance is maximized after the air pressure operation is terminated. In the example illustrated in FIG. 10, the air pressure difference (deviation) between the internal air pressure (air pressure C) of FPD 1 having the normal waterproof performance and the internal air pressure (air pressure D (C>D)) of FPD 1 having the deteriorated waterproof performance is maximized at time $t_{34}$ after time $t_3$ (at the time of air pressure operation termination).

Therefore, CPU 26 calculates, as the feature amount, the measured value (air pressure D) of the internal air pressure of FPD 1 at time $t_{34}$ after a lapse of a predetermined period of time from time $t_3$ at which the air pressure operation is terminated, and compares it with the corresponding measured value (air pressure C) of FPD 1 having the normal waterproof performance, thereby estimating the degree of the waterproof performance deterioration. By such processing being performed, the degree of the waterproof performance deterioration of FPD 1 can be estimated highly accurately. Note that, in a similar manner to the above, the measured values of FPD 1 having the normal waterproof performance (time $t_{34}$ and air pressure C) are stored in memory 27 in such a manner that measured values measured under the same conditions such as the opening degree of vent hole H and the peak value are set as a characteristic table, which are read by CPU 26 at the time of inspecting the waterproof performance.

Figure 11:
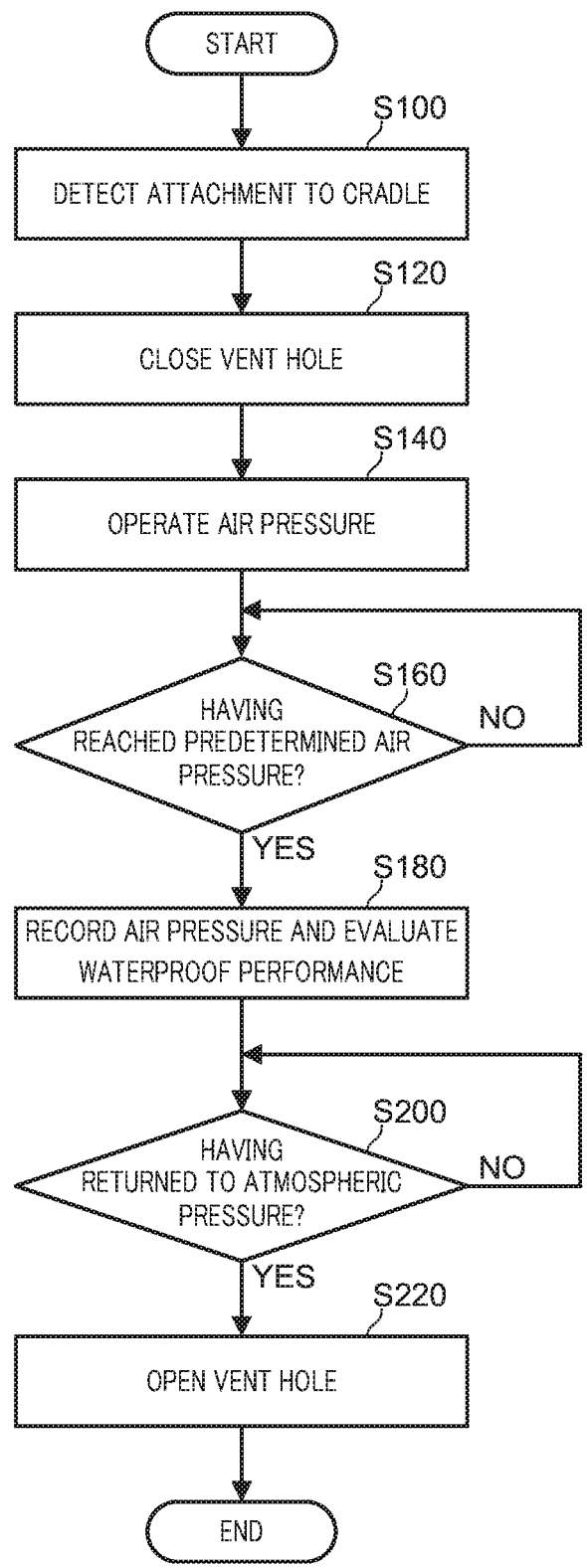
FIG. 11 is a flowchart related to measurement of the internal air pressure of the FPD according to the present embodiment.

Next, a process flow of the waterproof performance inspection performed by CPU 26 of FPD 1 in a case where FPD 1 is attached to cradle 5 and charged will be described with reference to the flowchart of FIG. 11.

As described above with reference to FIG. 3, when FPD 1 is attached to holder 51 of cradle 5, charging of the battery in casing 2 is started by the power (charging current) supplied from cradle 5 through connector 23. At this time, CPU 26 detects the charging current, or receives a connection signal output from cradle 5, for example, thereby detecting that FPD 1 is attached to cradle 5 (step S100).

Subsequently, CPU 26 outputs a control signal to the driving source of shutter 30, and controls the position of shutter 30 to close vent hole H of casing 2 (to seal vent hole H with shutter 30) (step S120). Through this process, the opening degree of vent hole H is minimized, and the air flow through vent hole H is prevented or substantially suppressed, whereby the airtightness of casing 2 is enhanced and the peak value of the internal air pressure at the time of air pressure operation can be secured.

In step S140, CPU 26 performs, while monitoring the output signal of air pressure sensor 28, various kinds of processing related to the air pressure operation for causing the internal air pressure of casing 2 to reach the peak value (positive peak pressure) described with reference to FIG. 8 and the like.

In one example, CPU 26 performs, as appropriate, processing for supporting the increase in the air pressure according to the charging environment of the battery or the like. For example, in a case where the charging is started with the battery whose capacity is substantially full, time required for completion of the charging is shortened, and the case where the internal air pressure does not reach the above-described peak value may occur. Therefore, CPU 26 obtains the amount (remaining amount) of the residual charge of the battery at the time of starting the charging and the estimated time required for completion of the charging, and in a case where there is a possibility that the internal air pressure does not reach the peak value before the completion of the charging, outputs an instruction to start the charging after discharge of the battery to cradle 5. Alternatively, CPU 26 may uniformly output the instruction described above to cradle 5 without checking the remaining amount of the battery.

In this manner, heat source 29 generates heat when the battery is charged after FPD 1 is attached to cradle 5 so that the temperature of the air inside casing 2 rises, whereby the internal air pressure of casing 2 gradually increases relative to the external air pressure (atmospheric pressure) as the temperature rises (see FIG. 6A).

When the charging of the battery is started, CPU 26 monitors the output signal of air pressure sensor 28, and determines whether the internal air pressure of FPD 1 has reached a preset peak value (step S160). When CPU 26 determines that the internal air pressure of FPD 1 has not reached a predetermined value (NO in step S160), the process returns to step S160 and the determination is repeatedly performed. On the other hand when CPU 26 determines that the internal air pressure of FPD 1 has reached the predetermined value (YES in step S160), the process proceeds to step S180.

In step S180, CPU 26 successively stores the values measured by air pressure sensor 28 in memory 27, records the transition (manner of changing) of the air pressure inside casing 2, and evaluates the waterproof performance of FPD 1 (casing 2) as described above on the basis of the measured values.

That is, CPU 26 corrects the minute variations of the values (raw data) measured by air pressure sensor 28 such that the variations are averaged (see FIG. 7), and compares the corrected value of the air pressure with data of the air pressure change characteristics of FPD 1 having the normal waterproof performance (see FIGS. 8 to 10), thereby evaluating the waterproof performance.

More specifically, CPU 26 determines whether deviation (singularity) in terms of the time, the inclination, and the air pressure variation width as described above with reference to FIGS. 9 and 10 has occurred in the corrected value of the air pressure relative to the air pressure change characteristics of FPD 1 having the normal waterproof performance. Then, when it is determined that the deviation (singularity) has occurred, CPU 26 displays a warning on indicator 24 or the like to the effect that the waterproof performance is deteriorated. On the other hand, when it is determined that the deviation (singularity) has not occurred, CPU 26 displays, on indicator 24 or the like, a message that the waterproof performance is normal. In this display processing, CPU 26 may alternatively or additionally transmit a message regarding the evaluation result of the waterproof performance (whether deterioration exists, etc.) to other devices included in X-ray imaging system 100 such as console device 3, host computer 4, and cradle 5 (peripheral device).

In step S200, CPU 26 determines whether the value of the air pressure measured by air pressure sensor 28 becomes equal to the atmospheric pressure. Then, while the measured value of air pressure sensor 28 indicates a value higher than the atmospheric pressure (NO in step S200), CPU 26 continues to evaluate the waterproof performance described above. On the other hand, when the measured value of air pressure sensor 28 indicates the atmospheric pressure (YES in step S200), CPU 26 terminates the evaluation of the waterproof performance and proceeds to step S220.

In step S220, CPU 26 drives the driving source (motor, etc.) of shutter 30 to control the position of shutter 30 such that vent hole H of casing 2 returns to the normal open state (closed state using shutter 30 is released), and then the series of the process is terminated.

Note that, as another timing in step S220, when the evaluation result of the waterproof performance of FPD 1 is obtained, the position of shutter 30 may be controlled by CPU 26 such that vent hole H of casing 2 is returned to the normal open state. In this case, the pressurized air in casing 2 can flow out to the outside through vent hole H, whereby the internal air pressure of casing 2 can be promptly returned to the atmospheric pressure.

Furthermore, as another exemplary control, after the internal air pressure of FPD 1 has reached the peak value, CPU 26 may control the position of shutter 30 even if the evaluation of the waterproof performance is being performed, thereby controlling the opening degree of vent hole H of casing 2 to open to a certain extent. In this case, although the accuracy of the waterproof performance estimation may be lowered depending on the opening degree of vent hole H as the airtightness of casing 2 is lowered during the waterproof performance evaluation, there is a merit that the result of the waterproof performance evaluation can be obtained earlier. When such control is performed, data of the result of measurement performed under the same conditions such as the timing of moving shutter 30 and the moving position (opening degree of vent hole H) with respect to the data of the characteristics of FPD 1 having the normal waterproof performance is stored in memory 27.

According to the present embodiment in which the process as described above is performed, the waterproof performance of FPD 1 can be quickly and accurately inspected while the user (medical personnel such as a doctor and a nurse) is not conscious in daily use.

In this manner, according to the present embodiment in which the flow rate of the air through vent hole H is controlled as FPD 1 is charged and the waterproof performance of casing 2 is automatically inspected, it becomes possible to substantially reduce labor, skill, human resources, and the like of the user necessary for inspecting the waterproof performance. In addition, the labor and the like required for the main users, namely, medical personnel such as a doctor and a nurse, is reduced, whereby the waterproof performance of FPD 1 can be quickly and highly accurately inspected while the medical personnel is not conscious in daily use in a medical site.

In the exemplary configuration described above, the case where CPU 26 automatically controls the position of shutter 30 at the time of adjusting the opening degree of vent hole H has been described. Meanwhile, various modifications are conceivable other than the above-described configuration for operating the opening degree of vent hole H of FPD 1 (configuration for regulating the flow rate of the air).

In the configuration described above with reference to FIG. 5, shutter 30 is disposed inside (inner surface side) casing 2, and the position is controlled by CPU 26. Meanwhile, shutter 30 may be disposed outside (outer surface side) casing 2, and the position may be manually operated. In this case, for example, vent hole H is provided in the upper region of casing 2 in FIG. 3 so that the user can manually move shutter 30 by sliding operation or the like. In the case of such a configuration, CPU 26 performs a display prompting the user to manually operate shutter 30 to close vent hole H in steps S120 and S220. In this case, although the labor of the user slightly increases at the time of inspecting the waterproof performance, the opening degree of vent hole H can be kept constant by one operation, whereby the user (doctor, etc.) can move to another hospital room or the like during the waterproof performance inspection. In addition, there is a merit that the driving source of shutter 30 becomes unnecessary and the cost can be reduced.

As another example, in the case where shutter 30 is disposed outside (outer surface side) casing 2 so that the position can be manually operated as described above, the driving source for driving shutter 30 may be provided on the side of cradle 5. In this case, CPU 26 may control the driving source on the side of cradle 5 in steps S120 and S220 after FPD 1 is attached to cradle 5.

Further, for example, vent hole H may be provided in the lower region of casing 2 in FIG. 3 (on the side surface facing holder 51 of cradle 5), and a member for changing the opening degree of vent hole H (opening degree control member) may be provided at the corresponding position of cradle 5 (holder 51). Examples of such an opening degree control member include an elastic cushion material such as rubber. With such a configuration being adopted, vent hole H is closed by the cushion material at the time of attaching FPD 1 to holder 51 of cradle 5, whereby effort of the user can be saved. Furthermore, a driving source of the cushion material may be provided in cradle 5, and the position of the cushion material relative to vent hole H may be changed so that the opening degree of vent hole H can be adjusted.

Figure 12:
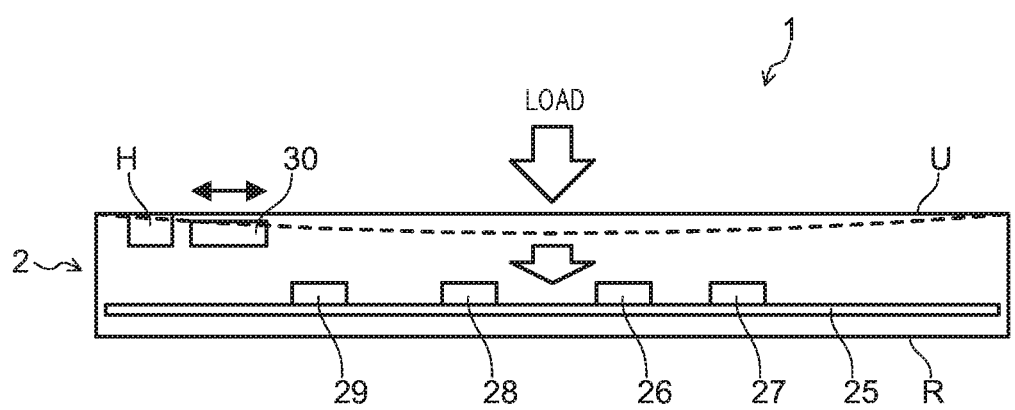
FIG. 12 is a diagram illustrating a further exemplary configuration for operating the internal air pressure of the FPD.

As another example for reducing the cost, as illustrated in FIG. 12, a part of back surface U of casing 2 may be formed of a flexible member so that the internal air pressure is operated using a jig such as a vise (not illustrated) or a weight having a predetermined weight. In this case, a part of back surface U forms a part of the air pressure operation section, and functions as a weight application section that elastically deforms when a load is externally applied. Such a configuration is considered to be effective also in the case of supporting the increase in the air pressure in step S140 described above.

In one example, when there is a possibility that the internal air pressure does not reach the peak value before the completion of the charging of the battery as described above, CPU 26 performs a display for prompting the user to press back surface U of casing 2 with a jig or the like. At this time, when CPU 26 monitors the output signal of air pressure sensor 28 and determines that the internal air pressure of FPD 1 has reached the preset peak value (YES in step S160), it performs a display for prompting the user to maintain the pressing state of the jig or the like. Thereafter, the user (doctor, etc.) can move to another hospital room for diagnosis or the like.

Further, a plurality of vent holes H of FPD 1 may be provided in casing 2. In a case where a plurality of vent holes H is provided in casing 2, at the time of inspecting the waterproof performance, the opening degree of only one vent hole may not be adjusted, for example, and the opening degree of the other vent holes may be operated by shutter 30. In this case, at the time of operating the internal air pressure, an air pump (not illustrated) is used as a peripheral device, and the air sent out from the air pump can be sent into casing 2 through the vent hole whose opening degree is not adjusted.

Note that, from the viewpoint of minimizing the labor of the user, in the case of providing the plurality of vent holes H to be opened and closed in casing 2, it is preferable that the opening degree of the plurality of vent holes H is operated by one shutter 30 at once when the configuration in which shutter 30 is manually moved is adopted. In this case, for example, the plurality of vent holes H to be opened and closed may be aligned on one surface of casing 2, and shutter 30 having a slit corresponding to the shape of vent hole H may slide (reciprocate) along the line.

In general, according to the present embodiment, it is not essential that vent hole H is completely closed at the time of inspecting the waterproof performance as long as the flow rate of the air through the vent hole at the time of inspecting the waterproof performance is sufficiently smaller than the flow rate of the air through vent hole H in the normal use. More specifically, it is permissible when the internal air pressure of casing 2 can reach the preset peak value by the air pressure operation described above, and vent hole H is closed (opening degree is decreased) to the extent that the difference from FPD 1 having the normal waterproof performance can be determined at the time of evaluation performed by CPU 26.

In the embodiment described above, the exemplary configuration in which, after the internal air pressure of casing 2 is increased (pressurized) to exceed the external air (atmospheric pressure) and reaches the positive peak value, the manner of decreasing the internal air pressure is measured to evaluate the waterproof performance has been described.

Figure 13:
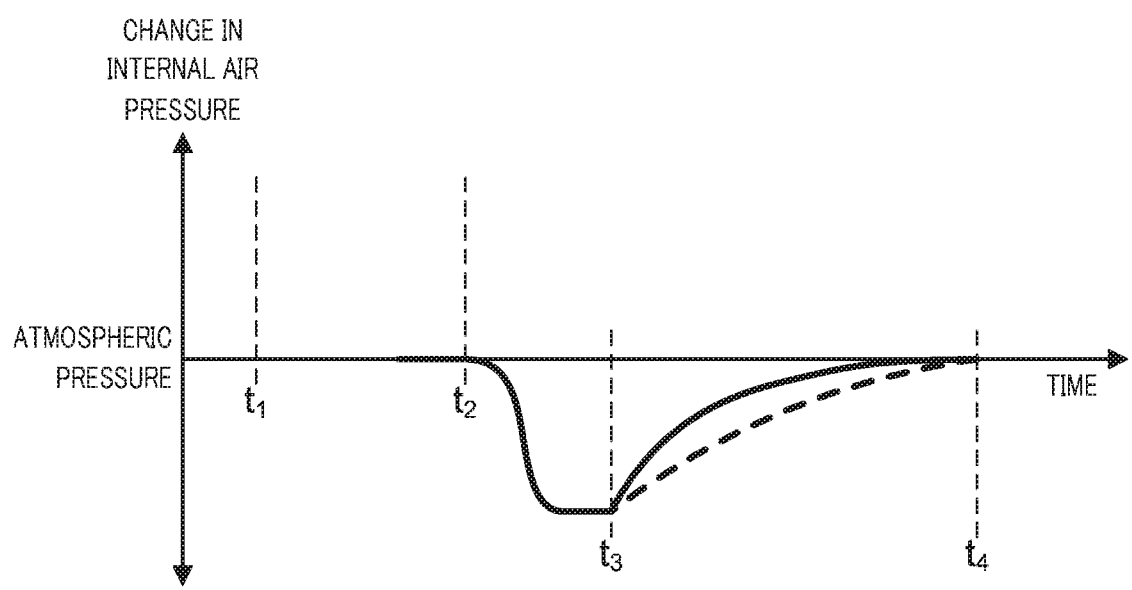
FIG. 13 is a characteristic graph for illustrating another method of measuring the internal air pressure of the FPD, which illustrates an exemplary case where a feature amount of a manner of rising of the internal air pressure of the FPD is extracted after the internal air pressure is depressurized to a negative peak value.

As another example, as illustrated in FIG. 13, after the internal air pressure of casing 2 is lowered (depressurized) below the atmospheric pressure to reach a negative peak value, a manner of increasing the internal air pressure (manner of changing to return to the atmospheric pressure) may be measured to evaluate the waterproof performance.

As a specific example in this case, a plurality of vent holes H is provided in casing 2, and CPU 26 causes shutter 30 to move to lower the opening degree of the plurality of vent holes H during the period from time $t_1$ at which FPD 1 is attached to cradle 5 to time $t_2$ at which the depressurization is started. Then, from time $t_2$, processing of air pressure operation for changing (in this example, depressurizing) the air pressure inside casing 2 is performed. In one example, the internal air of casing 2 is discharged (sucked out by the air pump) to the outside of casing 2 through vent hole H not to be opened and closed by shutter 30 using the air pump described above, thereby depressurizing the air inside casing 2.

Then, at time $t_3$ after the internal air pressure of casing 2 reaches the negative peak value, the processing of depressurization operation is stopped, and the charging of the battery of FPD 1 is started by cradle 5. Thereafter, as described above, the waterproof performance of FPD 1 is evaluated in a similar manner to the processing described above using the increase in the air pressure based on the heating (temperature rise) of the air pressure inside casing 2 caused by the heat radiation of heat source 29. That is, CPU 26 records the value of the internal air pressure (value detected by air pressure sensor 28) in the process in which the internal air pressure of casing 2 increases from the negative peak value toward the atmospheric pressure, and calculates the feature amount as described above.

Incidentally, since the atmospheric pressure in the world of nature constantly fluctuates, the atmospheric pressure at the time of starting the charging and the atmospheric pressure at the time of terminating the charging are not necessarily the same. Besides, since FPD 1 is easy to carry, charging may be performed while it is on the move by airplane, vehicle, and the like. When the atmospheric pressure fluctuates during the charging, it also affects the air pressure variation in casing 2. As a consequence, the quality of the waterproof performance may not be accurately determined in some cases.

Figure 14:
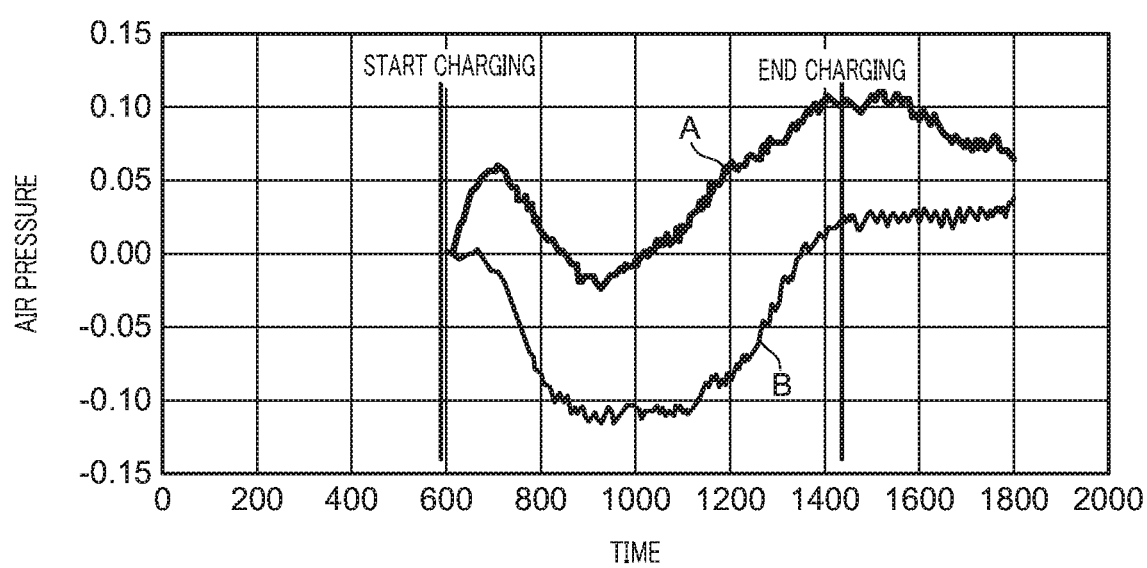
FIG. 14 is a graph illustrating a case where the FPD is charged in an environment where the atmospheric pressure fluctuates, which is a characteristic graph illustrating an example in which air pressure variation of each of the FPD having good waterproof performance and the FPD having deteriorated waterproof performance is averaged.

In response to such a problem, with respect to FPD 1 having good waterproof performance and FPD 1 having deteriorated waterproof performance, the present inventors repeatedly conducted an experiment of measuring the internal air pressure of each FPD 1 during the charging of each FPD 1 under the environment in which the atmospheric pressure fluctuates. As a result, it is found out that the air pressure variations converge by performing the processing of averaging variation values of the measured internal air pressure of FPD 1, and the difference between FPD 1 having good waterproof performance (characteristic A) and FPD 1 having deteriorated waterproof performance (characteristic B) is made clear as illustrated in FIG. 14. In FIG. 14, fluctuation characteristic A is a characteristic line obtained by averaging data obtained by measuring the internal air pressure of FPD 1 having good waterproof performance during the charging under various environments in which the atmospheric pressure fluctuates. On the other hand, fluctuation characteristic B is a characteristic line obtained by averaging data obtained by measuring the internal air pressure of FPD 1 having deteriorated waterproof performance during the charging under the environment same as the case of FPD 1 having good waterproof performance.

Therefore, as another example, CPU 26 may perform processing of averaging measured data of the internal air pressure of casing 2 at the plurality of times of charging, which is stored in memory 27, and may evaluate the waterproof performance of FPD 1 (casing 2) using the data having been subject to the averaging processing.

The averaging processing method described above is merely an example, and various methods for evaluating the waterproof performance of FPD 1 (casing 2) using the measured data of the internal air pressure of casing 2 at the plurality of times of charging can be adopted. For example, CPU 26 may analyze the measured data of the internal air pressure of casing 2 at the plurality of times of charging stored in memory 27 by machine learning or the like, and may extract singularity in terms of the air pressure variation width of casing 2 to evaluate the waterproof performance.

In the embodiment described above, an exemplary configuration in which the waterproof performance is inspected at the time when FPD 1 is attached to cradle 5 as a battery charger for charging the battery in FPD 1 is adopted. Meanwhile, it is also possible to adopt a configuration in which the waterproof performance is inspected at the time when FPD 1 is connected to another peripheral device other than cradle 5 (battery charger) such as the air pump described above. Furthermore, it is also possible to adopt a configuration in which the waterproof performance is inspected even when FPD 1 is not connected to a peripheral device.

As another specific example in the case where a part of back surface U of casing 2 is set as a weight application section and a plurality of vent holes H is provided in casing 2, an example in which the waterproof performance is inspected while surface R of FPD 1 is placed on a floor or the like without attaching FPD 1 to a peripheral device such as cradle 5 (see FIG. 12) will be described.

In this example, it is assumed that an inspection start instruction of the waterproof performance is input by user operation at time $t_1$ illustrated in FIG. 13. When the inspection start instruction of the waterproof performance is detected at time $t_1$, CPU 26 performs a display prompting the user to place a weight on back surface U of FPD 1. At this point of time, the position of shutter 30 remains in the initial state, and the opening degree of each vent hole H is in the maximum state.

Subsequently, when the weight is placed on back surface U of FPD 1, back surface U is elastically deformed downward by the self-weight of the weight (see arrow in FIG. 12), and the air of the amount according to the load of the weight is discharged to the outside of casing 2 through each vent hole H.

Thereafter, when an instruction to start the air pressure operation is input, CPU 26 having detected such instruction moves shutter 30 to lower the opening degree (flow rate of the air) of one or more vent holes H, thereby improving the airtightness of casing 2.

Subsequently, CPU 26 performs a display prompting the user to remove the weight placed on back surface U of FPD 1. Then, when the weight is removed (see time $t_2$ in FIG. 13), the load applied to back surface U of casing 2 is removed, whereby back surface U is displaced (restored) to return to the original shape. By this operation, the air density inside casing 2 decreases, and the internal air pressure of FPD 1 rapidly decreases.

When CPU 26 detects that the internal air pressure of casing 2 has reached the negative peak value (see time $t_3$), it records the value of the internal air pressure (value detected by air pressure sensor 28) in the process in which the internal air pressure of casing 2 increases from the negative peak value toward the atmospheric pressure, and calculates the feature amount as described above.

In this example, although the labor of the user is required at the time of operating the internal air pressure of casing 2, variations in the air pressure operation of each user can be suppressed by using the weight having a predetermined weight.

In the embodiment described above, CPU 26 of FPD 1 evaluates the waterproof performance. Meanwhile, the waterproof performance evaluation may be performed by a processor of another device included in X-ray imaging system 100, such as a processor of cradle 5 (battery charger), console device 3, and host computer 4. In this case, CPU 26 of FPD 1 may communicate with the processor via network N, base station 7, and the like, and may transfer required data such as a measured value of air pressure sensor 28 to the counterpart device.

The various exemplary configurations described above can be selected or combined as appropriate. For example, cradle 5 may be provided with the air pump described above, a mechanism for pressing the weight application section of back surface U with constant pressure, and the like. Further, cradle 5 described with reference to FIG. 3 is a vertical type in which FPD 1 is attached in the vertical direction. As another example of cradle 5, as illustrated in FIG. 12, FPD 1 may be a horizontal type in which FPD 1 is attached/detached in the lateral direction such that back surface U is on the upper side, and a mechanism for moving the weight described above with respect to back surface U may be added.

Although embodiments of the present invention have been described and illustrated in detail, the disclosed embodiments are made for purpose of illustration and example only and not limitation. The scope of the present invention should be interpreted by terms of the appended claims.

What is claimed is:

1. A radiographic imaging system, comprising:
   a radiographic imaging apparatus including a casing that houses a radiation detecting element that detects radiation with which a subject is irradiated and a battery, the casing being provided with a vent hole that circulates internal and external air; and
   a battery charger to which the radiographic imaging apparatus is to be attached and which charges the battery, wherein
   the radiographic imaging apparatus includes:
      an air pressure measurer that measures an internal air pressure of the casing, and
      a hardware processor that inspects, after the internal air pressure of the casing changes due to operation of pressure, waterproof performance of the radiographic imaging apparatus based on a changing aspect of the internal air pressure due to termination of the operation of the pressure, and
      wherein at least one of the radiographic imaging apparatus and the battery charger includes a flow rate regulator that reduces a flow rate of the air through the vent hole in a case where the radiographic imaging apparatus is attached to the battery charger.

2. The radiographic imaging system according to claim 1, wherein
   the hardware processor inspects the waterproof performance of the radiographic imaging apparatus based on a manner of changing of the internal air pressure measured by the air pressure measurer to return to atmospheric pressure after the internal air pressure of the casing is operated.

3. The radiographic imaging system according to claim 1, wherein
   the flow rate regulator includes an opening degree control member that operates to control an opening degree of the vent hole.

4. The radiographic imaging system according to claim 3, wherein
   the flow rate regulator includes a hardware processor that controls a position of the opening degree control member.

5. The radiographic imaging system according to claim 4, wherein
   the hardware processor controls the position of the opening degree control member to decrease the opening degree of the vent hole in a case where the casing is attached to the battery charger.

6. The radiographic imaging system according to claim 4, wherein
   the hardware processor controls the position of the opening degree control member to increase the opening degree of the vent hole after the waterproof performance is inspected.

7. The radiographic imaging system according to claim 3, wherein
   the opening degree control member is provided in the casing of the radiographic imaging apparatus.

8. The radiographic imaging system according to claim 3, wherein:
   the battery charger includes the opening degree control member, a holder that holds the casing of the radiographic imaging apparatus, and a power supplier that supplies charging power to the battery in a state where the casing is held by the holder, and
   the opening degree control member is configured to decrease the opening degree of the vent hole in a state where the casing is held by the holder.

9. The radiographic imaging system according to claim 3, wherein:
   a plurality of the vent holes are provided in the casing, and
   the opening degree control member is configured to operate the opening degree of at least one one of the vent holes.

10. The radiographic imaging system according to claim 1, wherein
    the radiographic imaging apparatus includes an air pressure operator that operates the internal air pressure of the casing.

11. The radiographic imaging system according to claim 10, wherein
    the air pressure operator includes a heat source that heats air inside the casing.

12. The radiographic imaging system according to claim 11, wherein
    the heat source is an electronic component to which current is applied as the battery is charged.

13. The radiographic imaging system according to claim 10, wherein
    the air pressure operator includes a weight applicator in which a part of the casing is elastically deformed by a load being applied from an outside of the casing.

14. A radiographic imaging apparatus including a casing that houses a radiation detecting element that detects radiation with which a subject is irradiated and a battery, the casing being provided with a vent hole that circulates internal and external air, and the radiographic imaging apparatus comprising:
    an air pressure measurer that measures an internal air pressure of the casing;
    a hardware processor that inspects, after the internal air pressure of the casing changes due to operation of pressure, waterproof performance of the radiographic imaging apparatus based on a changing aspect of the internal air pressure due to termination of the operation of the pressure, and a flow rate regulator that reduces a flow rate of the air through the vent hole in a case where the battery is charged.

15. A battery charger provided in a radiographic imaging apparatus including a casing that houses a radiation detecting element that detects radiation with which a subject is irradiated and a battery, the casing being provided with a vent hole that circulates internal and external air, the battery charger charging the battery, and the battery charger comprising:
   a holder that holds the casing of the radiographic imaging apparatus; and
   a flow rate regulator that reduces a flow rate of the air through the vent hole in a state where the casing is held.

16. A method of inspecting waterproof performance of a radiographic imaging apparatus including a casing that houses a radiation detecting element that detects radiation with which a subject is irradiated and a battery, the casing being provided with a vent hole that circulates internal and external air, and the method comprising:
   operating, in a case where the battery is charged, an internal air pressure of the casing in a state where a flow rate of the air through the vent hole is decreased by a flow rate regulator;
   measuring the internal air pressure after the operating; and
   inspecting the waterproof performance of the casing based on a changing aspect of the measured internal air pressure.

* * * * *